(12) United States Patent
Watling

(10) Patent No.: US 7,542,025 B2
(45) Date of Patent: Jun. 2, 2009

(54) INPUT APPARATUS FOR A COMPUTER SYSTEM

(76) Inventor: Michael J. Watling, 11 Cradock Street, Auckland 1007 (NZ)

( * ) Notice: Subject to any disclaimer, the term of this patent is extended or adjusted under 35 U.S.C. 154(b) by 177 days.

(21) Appl. No.: 10/506,166

(22) PCT Filed: Feb. 28, 2003

(86) PCT No.: PCT/NZ03/00038

§ 371 (c)(1),
(2), (4) Date: Apr. 28, 2005

(87) PCT Pub. No.: WO03/075144

PCT Pub. Date: Sep. 12, 2003

(65) Prior Publication Data

US 2005/0219201 A1 Oct. 6, 2005

(30) Foreign Application Priority Data

Mar. 1, 2002 (NZ) .................. 517510

(51) Int. Cl.
*G09G 5/00* (2006.01)

(52) U.S. Cl. .................. 345/156; 715/810
(58) Field of Classification Search ......... 345/156–160, 345/168, 173; 715/773, 810, 835, 856, 863, 715/865, 859
See application file for complete search history.

(56) References Cited

U.S. PATENT DOCUMENTS

| | | | |
|---|---|---|---|
| 4,713,535 A | 12/1987 | Rhoades | |
| 4,908,612 A * | 3/1990 | Bromley et al. | 345/159 |
| 5,056,059 A * | 10/1991 | Tivig et al. | 715/828 |
| 5,347,295 A * | 9/1994 | Agulnick et al. | 345/156 |
| 5,515,079 A * | 5/1996 | Hauck | 345/157 |
| 5,524,196 A | 6/1996 | Blades | |
| 5,701,424 A | 12/1997 | Atkinson | |
| 5,745,717 A | 4/1998 | Vayda et al. | |
| 5,926,178 A | 7/1999 | Kurtenbach | |
| 6,097,373 A | 8/2000 | Jakobs | |
| 6,262,717 B1 * | 7/2001 | Donohue et al. | 345/173 |
| 2003/0107607 A1 * | 6/2003 | Nguyen | 345/863 |

FOREIGN PATENT DOCUMENTS

| | | |
|---|---|---|
| EP | 0 498 082 A1 | 8/1991 |
| WO | 96/30822 | 10/1996 |

* cited by examiner

*Primary Examiner*—Bipin Shalwala
*Assistant Examiner*—Kenneth B Lee, Jr.
(74) *Attorney, Agent, or Firm*—Lowe Hauptman Ham & Berner, LLP

(57) ABSTRACT

The present invention relates to an input apparatus for a computer system which includes a pointer device operable by a user, a symbol display system adapted to display a plurality of symbols to a user, and one or more pointer selection sensors adapted to sense the selection of one or more symbols by the pointer device. The symbol display system is adapted to display a plurality of input symbols and at least one commit symbol, whereby selection of a commit symbol by the pointer device will cause the last input symbol selected to be supplied by an associated computer system as input. The invention may be particularly suitable for use by members of the disabled and/or aged community.

16 Claims, 3 Drawing Sheets

INPUT APPARATUS FOR A COMPUTER SYSTEM

RELATED APPLICATIONS

The present application is based on International Application No. PCT/NZ03/00038, filed Feb. 28, 2003, and claims priority from, New Zealand Application Number 517510, filed Mar. 1, 2002, the disclosure of which is hereby incorporated by reference herein in its entirety.

TECHNICAL FIELD

This invention relates to an input apparatus for a computer system. Preferably the present invention may improve the speed at which commands or selected symbols may be inputted into a computer system without the need for a standard keyboard. Preferably the present invention may also be used to improve the ease with which disabled persons can input information or commands into a computer system. Reference throughout this specification will also be made to the input apparatus being used to supply input to a computer system, but those skilled in the art should appreciate that other types of equipment may also be supplied input using the present invention if required.

BACKGROUND ART

Manual or user input devices for computer systems are normally implemented through a standard keyboard and/or mouse arrangement. A user presses a selected key on the keyboard to transmit an input character to the computer system. Alternatively a user can adjust the position of the mouse to move a cursor on a computer display and activate one of its buttons to select objects or elements displayed.

However, some people find keyboards difficult to use. A degree of manual dexterity is required to achieve both accuracy and speed of operation for keyboard data entry into a computer system. Proficiency in keying only comes after a significant amount of practice or training, and is therefore a barrier to some persons using a computer system. Furthermore, disabled persons can find it difficult to use a keyboard due to the level of manual dexterity required. The speed and accuracy with which input can be supplied to a computer system can be limited for a disabled user employing a standard keyboard.

Mouse pointers are more readily used and accepted by the public at large. However, there are some limits with regard to the scope of commands or input data which can be supplied easily using a mouse. The actual input characters or symbols which can be selected by a user with a mouse will be determined by what the system is capable of presenting on a display screen to a user. Disabled persons may also find it difficult to effectively use a mouse, which requires accurate placement of a mouse pointer and also a synchronised depression of one of the mouse buttons when an object or symbol to be selected is under the mouse pointer.

Therefore, it would be preferable to have an input apparatus for a computer system which could be readily and easily used by unskilled persons or those with limited manual dexterity. It would be preferable to have an input apparatus which could be used easily to provide both accurate and fast input to a computer system, without necessarily the need for a standard keyboard or mouse arrangement.

Attempts have been made to address these deficiencies in standard keyboard and mouse combinations, such as the apparatus' discussed in U.S. Pat. No. 6,097,373 (to Jakobs), and U.S. Pat. No. 4,713,535 (to Rhoades). These patent specifications describe laser, infrared or light based pointer systems which are worn on a headband by a user. The user trains the pointer on a particular symbol displayed on a keyboard, where the dwelling time of the pointer beam on a symbol displayed indicates that particular symbol has been selected and it is therefore supplied as input to a computer system.

However, these types of systems still do not completely address the dexterity requirements for an input system. A user must accurately position the pointer beam on a symbol to be selected and then hold the pointer beam in place for the correct dwell time to ensure that the symbol is selected and supplied as input to a computer system. Furthermore, the requirement for a dwell time period to be observed slows down the operation of such systems, thereby reducing the speed at which input data can be supplied to the computer system. In addition, there is no optimisation of key or symbol arrangements which are to be selected by a user. Relatively slow data input times are inherent in such systems with specific key or symbol combinations located at opposite ends or areas of the symbol keyboard.

An improved input apparatus for a computer system which addressed any or all of the above problems would be of advantage. An input apparatus which was easy to use and which could supply input to a computer system both accurately and quickly would be of advantage. An input apparatus which limited the need for co-ordination or manual dexterity in a user would also be of advantage.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided an input apparatus for a computer system which includes, a pointer device operable by a user, and a symbol display system adapted to display a plurality of symbols to a user, and one or more pointer selection sensors adapted to sense the selection of one or more symbols by the pointer device, where the symbol display system is adapted to display a plurality of input symbols and at least one commit symbol, whereby selection of a commit symbol by the pointer device will cause the last input symbol selected to be supplied to an associated computer system as input.

According to a further aspect of the present invention there is provided an, input apparatus substantially as described above wherein the pointer device is adapted to emit electro-magnetic radiation, and a pointer selection sensor is adapted to detect said emitted electro-magnetic radiation to sense symbol selection by the pointer device.

According to a further aspect of the present invention there is provided an input apparatus substantially as described above wherein the pointer device is adapted to emit a laser beam and/or an infrared energy beam.

According to yet another aspect of the present invention there is provided an input apparatus for a computer system wherein the symbol display system is adapted to display input symbols in at least one array which defines a circuit.

According to a further aspect of the present invention there is provided an input apparatus for a computer system wherein one or more commit symbols are displayed in an array outside of the area defined by a circuit of input symbols.

According to yet another aspect of the present invention there is provided an input apparatus substantially as described above wherein the symbol display system is adapted to display at least one commit symbol within an area bounded by a circuit of input symbols.

According to a further aspect of the present invention there is provided an input apparatus for a computer system substantially as described above, wherein the symbol display is adapted to display at least one commit symbol at substantially the centre or the focus or focuses of a circuit of input symbols displayed.

According to yet another aspect of the present invention there is provided an input apparatus for a computer system substantially as described above wherein the symbol display system is adapted to display at least one substantially elliptical or substantially circular circuit of input symbols.

The present invention is adapted to provide an input apparatus for a computer system. Such an input apparatus may preferably emulate the functions of and potentially replace a standard keyboard and/or mouse arrangement for a computer system. Such an input apparatus may provide screen pointer information in preferred embodiments in addition to input symbol or key selection inputs to the computer system.

Reference throughout this specification will also be made to the present invention being used as an input apparatus for a computer system. However, those skilled in the art should appreciate that the input apparatus provided may also be used to provide input to other forms of equipment which need not necessarily be computer systems. For example, in one alternative embodiment the input apparatus provided may be used an input system for a vehicle, or for process control machinery in a factory for example.

In a further preferred embodiment an input apparatus may be provided as a plug-in replacement to a standard keyboard and/or mouse combination. Such an input apparatus may utilise the standard plug connectors provided in a computer system to connect a keyboard or mouse to same. For example, the input apparatus may be designed in a preferred embodiment to connect to a computer system using standard keyboard and mouse connectors, and may also be adapted to send input signals to the computer system using substantially the same schemes or protocols as those employed by standard keyboards or mice.

This configuration of the invention allows the input apparatus to entirely replace a standard keyboard and mouse input arrangement and also to be installed within substantially any type of pre-existing computer system without the need for special software, drivers or adaption hardware.

Preferably the input apparatus includes a symbol display system which is adapted to display a plurality of symbols to a user. These symbols may be selected by a pointer device to allow a user to send input to an associated computer system.

Preferably the display system will display a plurality of input symbols to a user. Input symbols may represent specific types of input for a computer system such as for example, standard key strokes from a computer keyboard. Alternatively, such input symbols may be provided as graphical icons which can represent a complex sequence of commands or input to a computer system. For example such icons could represent control buttons for industrial machinery or other types of equipment which may require computerised control.

In a further preferred embodiment input symbols may be displayed which represent movement commands for a cursor on a display screen. Such input symbols may represent a particular direction in which the cursor is to be moved through the selection of that particular symbol by a user.

Reference throughout the specification will also be made to input symbols displayed by a symbol display system being standard characters normally printed on an existing keyboard. However, those skilled in the art should appreciate that other types of input symbols may also be displayed in conjunction with the present invention and reference to the above only throughout this specification should in no way be seen as limiting. For example, in other embodiments characters or letters from different alphabets, symbol construction components for Asian languages or alternatively icons representing basic commands or a sequence of commands may also be displayed as input symbols in accordance with the present invention.

In a preferred embodiment the symbol display system may be formed as or incorporate a substantially flat surface which displays graphics representing the symbols to be selected. Furthermore, the interior or internal components of the symbol display system may also incorporate the plurality of selection sensors required to operate the present invention.

Furthermore, such a symbol display system may be formed as or incorporate a liquid crystal display unit adapted to display graphics representing the symbols to be selected. Alternatively, the symbol display system may be formed from or incorporate touch sensitive surfaces which will enable a user to touch graphics representing symbols to effect the selection of same.

In a further preferred embodiment the face of the display system may also incorporate light emitting diodes or other small light emitting systems associated with pointer selection sensors, which are illuminated when a particular symbol has been selected by the pointer device.

In some embodiments the symbol display system may also be encased within a waterproof or airtight housing where it is to be used in potentially hazardous or corrosive environment. Preferably as symbols can be selected through the transmission of electro-magnetic beams there is no need for any components of the symbol display system to protrude out from such a waterproof or airtight housing. This allows the present invention to be configured for use in relatively harsh environments which would normally damage or degrade the performance of existing keyboards or mice.

Reference throughout this specification will also be made to the symbol display system as having a display face with a number of static symbols displayed on same. However those skilled in the art should appreciate that other configurations of this component are envisioned and reference to the above only throughout this specification should in no way be seen as limiting. For example, in other embodiments the symbols displayed may change through use of a screen or projection system employed to form a portion of the symbol display system if required.

Preferably the display system provided may also be adapted to display at least one commit symbol. The selection of a commit symbol can be employed by a user to confirm that a previously selected input symbol should actually be sent to the associated computer system as input.

A commit symbol can be employed to improve the accuracy with which inputs can be supplied to a computer system used in the present invention. A selected input symbol may only be supplied as input once the user has also selected a confirmation symbol which will trigger the transmission of the required input. As a significant amount of time is spent correcting missed keys with the standard keyboards, the applicant's feel that this feature of the invention may substantially improve the accuracy of the input apparatus provided.

Preferably the input apparatus also includes a pointer device which is employed by a user to select symbols displayed by the symbol display system. Such a pointer device may be moved or operated by a user to place a visual cursor or pointer over a displayed symbol which is to be selected.

Preferably the input apparatus device also includes at least one pointer selection sensor. Such a sensor or sensors may preferably sense the selection of a particular symbol when the pointer cursor is placed over or on a particular symbol. In a further preferred embodiment the input apparatus may include a plurality of pointer selection sensors, with a sensor for each symbol displayed by the symbol display system. This configuration of the invention allows fine and accurate determinations to be made with regard to which a range of symbols have been selected by a user.

In a preferred embodiment the pointer device may be adapted to emit at least one beam of electro-magnetic radiation. Furthermore, any pointer selection sensors employed by the present invention may also be adapted to sense the targeting of a particular symbol by a beam of electro-magnetic radiation emitted by the pointer device.

In a further preferred embodiment the pointer device may emit electro-magnetic radiation, which, when directed to a displayed symbol will give the user of the apparatus a visual indication or cue confirming that they have trained the pointer device onto a particular symbol. Such a visual clue may be provided through electro-magnetic radiation which is not necessarily sensed by any pointer selection sensors but may simply give the user visual cues to operate the present invention with.

Alternatively, in another embodiment a pointer selection sensor or sensors may incorporate components which give a user a visual cue that a particular symbol has been selected. For example, in one embodiment a pointer selection symbol may include a small light source such as a light emitting diode which will be illuminated when the sensor detects that the particular symbol involved has been targeted by the user's pointer device.

In a further preferred embodiment the pointer device may be adapted to emit a laser beam to illuminate and/or select a particular symbol displayed by the symbol display system. A laser beam will also give a user a visual cue with regard to which areas or symbols of the symbol display system they have trained the pointer beam on and therefore selected.

However, in other embodiments alternative forms of electro-magnetic radiation may be emitted by the pointer device. For example, in an alternative embodiment beams of tightly focussed infrared energy can be employed if required.

Those skilled in the art should appreciate that many different configurations of the present invention are possible in this regard and reference to one particular scheme only throughout this specification should in no way be seen as limiting. For example, in one alternative embodiment a combination of visual cues from both a pointer device and pointer selection sensors may be given to a user.

Furthermore, those skilled in the art should also appreciate that the pointer device need not necessarily emit electro magnetic radiation to be detected by at least one pointer selection sensor. For example, in alternative embodiments a pointer device may emit a magnetic field which is detected by a selection sensor or alternatively physical contact or close proximity of the pointer device to a selection sensor may be employed in the operation of the present invention. In yet another embodiment, physical components of a pointer device may block the passage of ambient light to a selection sensor, thereby indicating selection of a symbol.

Those skilled in the art should appreciate that use of optical based systems substantially as described above in the implementation of the pointer device should in no way be seen as limiting.

In a preferred embodiment the pointer device may also include a mounting system which allows it to be worn on the body of the user. For example, in one further preferred embodiment the pointer device may be mounted on the head apparel, such a head band, or a set of glasses frames worn by a user. This will position the pointer beam or cursor to tall on the symbol display system approximately the same position at which the user's eyes are focussed and their head is orientated.

However, in alternative embodiments the pointer device need not necessarily be mounted on nor worn by a wearer. For example, in one alternative embodiment the pointer device may be configured as a hand held element which a user can move over the symbol display system to select a particular symbol. In yet another alternative embodiment the pointer device may be mounted within or formed to resemble a standard computer mouse which can be moved over the surface of the symbol display system to select particular symbols. Providing a mouse-like apparatus for use with the present invention can improve the user's familiarity with the components employed and potentially improve the user's willingness to use the present invention.

Reference throughout this specification will also be made to the pointer device being adapted to emit a laser beam and also being configured to be worn by a wearer using head apparel such as a head band. However, those skilled in the art should appreciate that other configurations of the present invention are envisioned, and reference to the above only throughout this specification should in no way be seen as limiting.

An input apparatus as configured in a preferred embodiment may be easily employed by a user to provide input to a computer system. To select a particular symbol as computer input the user may initially train the pointer device on the required symbol represented by the symbol display system. Preferably once the symbol has been illuminated by the pointer device's laser beam, a light emitting diode controlled by a pointer selection sensor for that symbol will be illuminated, giving the user an indication that they have correctly selected the symbol involved.

At this stage the user will then need to confirm the correct input symbol has been selected through in turn selecting a commit symbol. The same process again will be executed to indicate that a commit symbol has been selected and therefore the last input symbol selected has been supplied to the associated computer system as input.

In a preferred embodiment the input symbols displayed by the symbol display system may be arranged in at least one array which defines a circuit. A circuit may be defined for the purposes of this specification as an arrangement which defines a route or course. The symbols involved may trace a path across the face of the symbol display system to fully enclose an area of same.

In a further preferred embodiment at least one commit symbol may be displayed or located within a circuit defined by an array of input symbols. Providing one or more commit symbols to the interior of such a circuit minimises the distance over which the pointer device must be moved to confirm the selection of a particular symbol.

However, in an alternative embodiment one or more commit symbols may be located outside of an area defined by a circuit of input symbols. Such a commit or commit symbols may be placed relatively close to the displayed input symbols to again preferably minimise the distance which the pointer device has to be moved to confirm the selection of an input symbol.

In a further preferred embodiment a commit symbol may be located substantially in the centre, or a focal point or focus of an area defined by a circuit of input symbols. A commit symbol may be placed substantially in the centre of such an array or alternatively at a focus or focal point of the array—with this location being the closest point to a significant number of input symbols displayed within the array involved. Providing a commit symbol in such a location substantially improves the speed and accuracy with which the present invention may be used. This positioning of a commit symbol minimises its distance from all or a substantial number of the symbols displayed in the array, thereby minimising the amount of movement of the pointer device required to select a sequence of symbols.

In a further preferred embodiment an array of input symbols may be formed as a substantially circular or elliptical circuit. This provides a relatively regular array of input symbols which define an area in which one or more commit symbols may be located. In the case of a circular array a single commit symbol may be located substantially at the centre of the circle defined, whereas with an elliptical array with a pair of foci, a commit symbol may preferably be placed at each of the foci involved.

Reference throughout this specification will also be made to a single commit symbol only being located substantially within the centre of each array of input symbols provided. Reference throughout this specification will also be made to input symbols being provided in substantially circular arrays with a single commit symbol being located at the centre of such circular arrays. However, those skilled in the art should appreciate that other configurations of the layout of input symbols and commit symbols are envisioned and reference to the above only throughout this specification should in no way be seen as limiting. Array shapes other than a circle or ellipse may also be used in conjunction with the present invention if required.

In a preferred embodiment a series of input symbol arrays may be located on the display face of the display symbol system. Furthermore, other symbols available for selection need not necessarily be applied or marked out within the arrays defined in some instances.

In a further preferred embodiment the display face of the symbol display system may have three distinct circular arrays of input symbols marked upon it. A primary array of alphabetic characters may form the first array while an array of numeric and mathematical characters may form the second array. A third array may be formed from punctuation and page navigation and formatting characters in such an embodiment.

In a further preferred embodiment screen cursor input symbols may also be displayed, preferably again a substantially circular array of input symbols. Input symbols may be provided to move a screen cursor up, down, left, right or any other required direction through the selection of a particular input symbol.

The present invention may provide many potential advantages over the prior art.

The input apparatus described above may be used to fully replace a standard keyboard and/or mouse arrangement for an existing computer system. The apparatus involved may be provided as a plug-in component which uses the same connectors and communication protocols as a standard computer keyboard and/or mouse.

The present invention may allow relatively accurate and fast input to be generated by those without a high degree of manual dexterity or co-ordination. The applicants believe that the present invention may provide significant advantages to those in the disabled community wishing to interact with computer systems.

Providing input symbols are arrayed in circuits and preferably in circular arrays substantially increases the accuracy and speed at which the present invention may be employed. As the distance to which the user needs to move the pointer device is reduced through the provision of a commit symbol substantially in the centre of such a circuit, this increases the speed at which symbols can be selected and then confirmed as input.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1A:
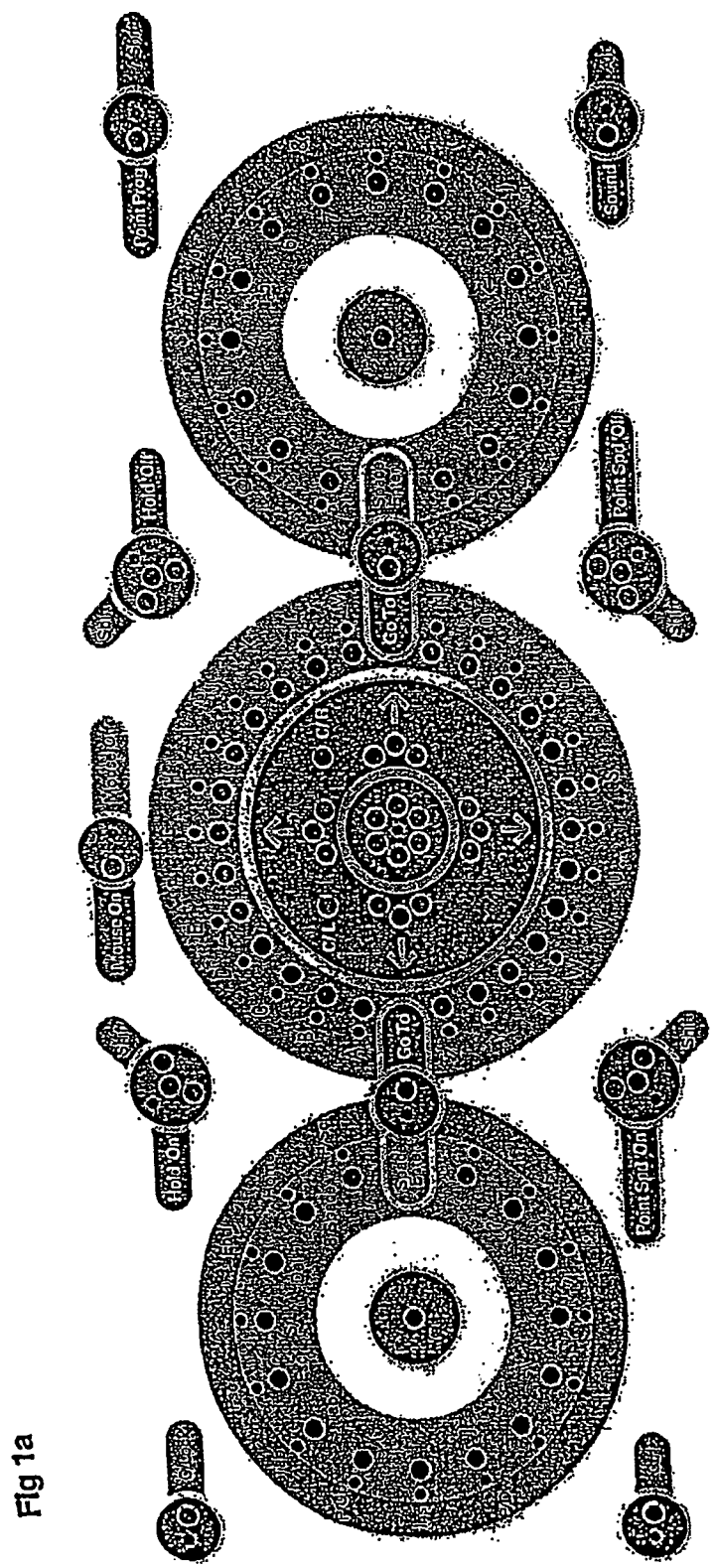
FIG. 1a shows a top view of the display face for a symbol display system as configured in accordance with the preferred embodiment of the present invention.

FIG. 1a shows the front display face of a symbol display system as incorporated within an input apparatus provided in accordance with the preferred embodiment. The display face has a plurality of input symbols marked on its surface which are arrayed in three circuits with a substantially circular shape. Each of the input symbols displayed may be selected by a laser pointer device (not shown) to provide input to a computer system to which the input apparatus is connected.

Also shown in the centre of each circular array is a commit symbol which again can be selected by an associated pointer device. The commit symbol can be used to conform that a selected input symbol is definitely to be supplied to a computer system as input. When a commit symbol is selected the last selected input symbol can be provided to the computer system as an input.

Figure 1B:
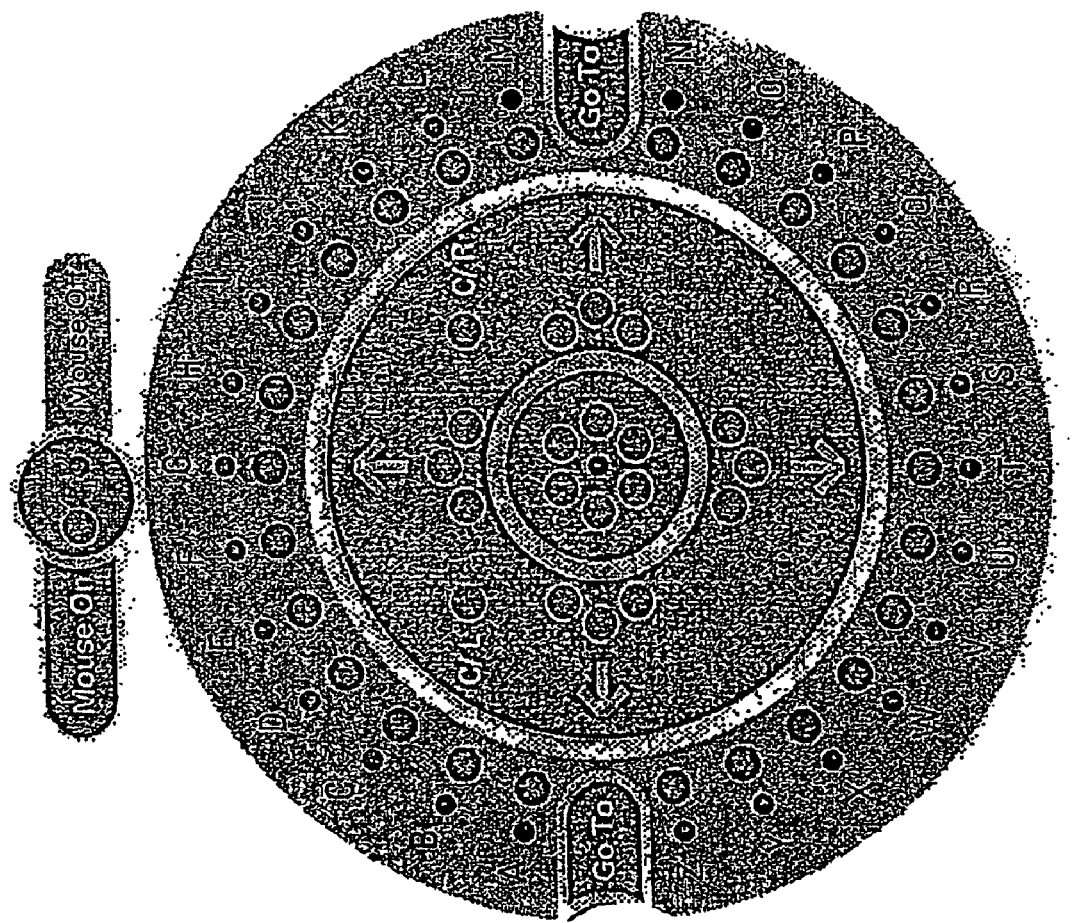
FIG. 1b shows the magnified view of the central circuits of display symbols shown with respect to FIG. 1a, and FIG. 2 shows a track of movements made by a pointer device used in accordance with the preferred embodiment to supply the word shown as input to a computer system.

FIG. 1b shows more clearly the central array shown with respect to FIG. 1a. With the array shown in FIG. 1b the letters of the Roman alphabet are displayed, which can be selected by a user to build up text input for a computer system. Also shown next to each input symbol is the sensing component of a pointer selection sensor. In the embodiments shown with respect to FIGS. 1a and 1b, a pointer device operated by a user can be trained on an input symbol to select same. The associated pointer selection sensor will then detect the emitted laser light to trigger the selection of the input symbol involved. Such pointer selection sensors also include a light emitting diode which is illuminated when the sensor determines that the pointer device laser beam has been trained on the associated input symbol.

In the embodiment shown with respect to FIGS. 1a and 1b the input symbols are arrayed in circular patterns with commit symbols in the centre. Numerous input symbols are displayed from the letters of the Roman alphabet in the central array, to the numbers 0 to 9 and mathematical operators being displayed in the right most array. Page formatting and punctuation input symbols are displayed in the left most circular array of input symbols. The central array also includes a further internal or interior array of input symbols which give commands to move a cursor on a display screen associated with a computer system. These input symbols can be selected to move a screen cursor up, down, left or right depending on the particular symbol selected.

The provision of circular arrays of input symbols reduces the distance which a user has to move the laser pointer device to select and then confirm a collection of input symbols as input to a computer system. The central positioning of the commit symbols minimises the distance which the pointer device has to be moved to confirm input symbol selection. Furthermore, the provision of a commit symbol can substantially improve the accuracy with which the input apparatus can be used, as false symbol selections will not be confirmed by a user but instead corrected before being sent as input.

The present invention will provide users with the ability to provide as input to a computer system on average at least twenty to thirty words per minute. Such a word input speed is far greater than for input devices which typically provide input speeds of between five and fifteen words per minute.

For example, the British Journal of Occupational Therapy (June 1988 51(6)) states:

"Although more and more disabled people are benefiting from microcomputer technology, an operating speed of more than 5-10 wpm with an alternative input device is rarely achieved".

Furthermore, the ability to increase the reaction speed of the apparatus components of the present invention will facilitate word input speeds of at least forty words or more per minute.

Figure 2:
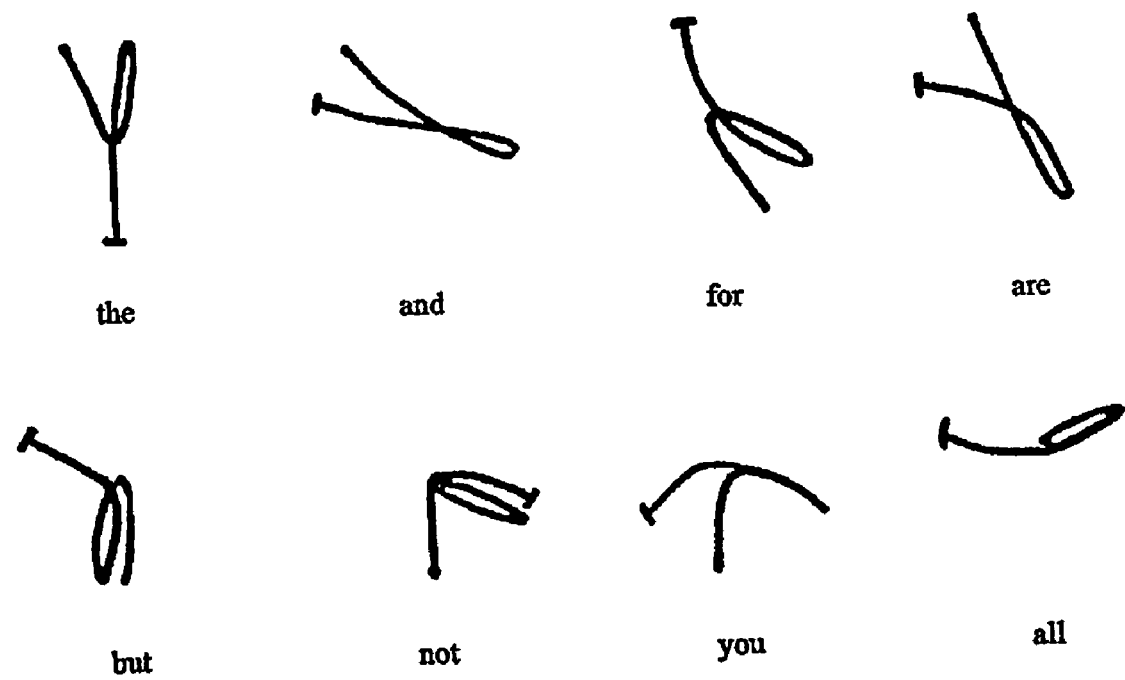

FIG. 2 illustrates these characteristics of the input apparatus through a track of the movements made by the pointer device to select and confirm as input collection of characters making up common English language words. As can be seen from FIG. 2, the track of the pointer device passes across the central commit symbol for each selected input symbol where a large number of instances the next character or input symbol in the sequence to be selected is on the opposite side of the array of symbols displayed.

Aspects of the present invention have been described by way of example only and it should be appreciated that modifications and additions may be made thereto without departing from the scope thereof as defined in the appended claims.

The claims defining the invention are:

1. An input apparatus for a computer system which comprises:
    a pointer device operable by a user, and
    a symbol display system that displays a plurality of input symbols to a user, where said plurality of input symbols represent characters and/or pictogram information content, the symbol display system displaying an array of input symbols defining at least one circuit, and
    one or more pointer selection sensors configured to sense the selection of a symbol by the pointer device,
    where the symbol display system also displays at least one commit symbol, said at least one commit symbol being displayed at substantially the center of the focus of an array of input symbols,
    whereby the input apparatus is configured such that the at least one circuit of input symbols is arranged in a substantially elliptical or circular arrangement such that the user can select a signal input symbol using the pointer device, and directly move the pointer device to the commit symbol without traversing other input symbols such that selection of the commit symbol by the pointer device causes the previous single input symbol only selected by the pointer device to be sent to the computer system.

2. An input apparatus as claimed in claim 1, wherein the pointer device is configured to emit a beam of electromagnetic radiation.

3. An input apparatus as claimed in claim 1, wherein the pointer device is operated by a user to place a visual cursor over a displayed symbol which is to be selected by said user.

4. An input apparatus as claimed in claim 2, wherein the directing of the beam of electromagnetic radiation emitted from the pointer device onto an input symbol displayed by the symbol display system provides the user with a visual indication confirming that said beam has been trained onto said input symbol.

5. An input apparatus as claimed in claim 1, wherein the pointer device includes a mounting system.

6. An input apparatus as claimed in claim 5, wherein the mounting system is configured to be removably attached to the body of a user.

7. An input apparatus as claimed in claim 5, wherein the mounting system is configured to enable the pointer device to be mounted on head apparel or a set of glass frames worn by a user.

8. An input apparatus as claimed in claim 1, wherein the pointer device is configured as a hand held element.

9. An input apparatus as claimed in claim 8, wherein the hand held element is formed as a standard computer mouse.

10. An input apparatus as claimed in claim 1, wherein the symbol display system is formed as or incorporates at least one substantially flat surface which displays graphics representing symbols.

11. An input apparatus as claimed in claim 10, wherein said at least one surface of the symbol display system displays at least three distinct substantially circular arrays of input symbols.

12. An input apparatus as claimed in claim 10, wherein said at least one surface of the symbol display system incorporates light emitting diodes.

13. An input apparatus as claimed in claim 1, wherein at least one screen cursor input symbol is displayed by the symbol display system.

14. An input apparatus as claimed in claim 13, wherein a screen cursor input symbol represent movement commands for a cursor on a display screen.

15. An input apparatus as claimed in claim 1, wherein the pointer selection sensor incorporates components configured to provide a user with a visual cue that a particular symbol has been selected.

16. An input apparatus as claimed in claim 1, which includes screen pointer information.

* * * * *